United States Patent [19]

Inoue et al.

[11] Patent Number: 4,693,844
[45] Date of Patent: Sep. 15, 1987

[54] VINYLNORBORNYL ALCOHOL AND PERFUME COMPOSITION CONTAINING THE SAME

[75] Inventors: Yoshiharu Inoue, Osaka; Fumio Tanimoto, Kyoto; Hisao Kitano, Osaka, all of Japan

[73] Assignee: Nippon Petrochemicals Company Limited, Tokyo, Japan

[21] Appl. No.: 801,098

[22] Filed: Nov. 22, 1985

[30] Foreign Application Priority Data

Nov. 27, 1984 [JP] Japan ................ 59-250311

[51] Int. Cl.$^4$ .......... A61K 7/46; C11B 9/00; C07C 35/22
[52] U.S. Cl. ............ 512/14; 568/820; 568/821; 512/4
[58] Field of Search ............ 252/522 R; 568/820, 568/821

[56] References Cited

U.S. PATENT DOCUMENTS

| | | | |
|---|---|---|---|
| 3,860,653 | 1/1975 | Kitvhen | 568/820 |
| 3,927,116 | 12/1975 | Rick et al. | 568/820 |
| 4,224,253 | 9/1984 | Baumann et al. | 568/820 |
| 4,524,017 | 6/1985 | Inoue et al. | 568/445 |
| 4,604,488 | 5/1986 | Fujikura et al. | 568/820 |

FOREIGN PATENT DOCUMENTS

| | | | |
|---|---|---|---|
| 2843838 | 4/1980 | Fed. Rep. of Germany | 568/820 |
| 3319740 | 12/1983 | Fed. Rep. of Germany | 568/820 |
| 0126238 | 7/1985 | Japan | 568/820 |
| 0185737 | 9/1985 | Japan | 568/820 |

*Primary Examiner*—Werren B. Lone
*Attorney, Agent, or Firm*—Scully, Scott, Murphy & Presser

[57] ABSTRACT

A vinylnorbornyl alcohol of 5- or 6-vinyl-2-hydroxymethylbicyclo[2.2.1]heptane which is represented by the following structural formula:

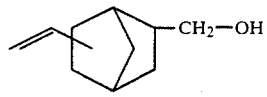

The compound has particular fragrance of a mint-like note partaking of camphor tone.

2 Claims, No Drawings

VINYLNORBORNYL ALCOHOL AND PERFUME COMPOSITION CONTAINING THE SAME

BACKGROUND OF THE INVENTION (1) Field of the Invention

This invention relates to vinylnorbornyl alcohol. More particularly, the invention relates to 5- or 6-vinyl-2-hydroxymethylbicyclo[2.2.1]heptane and perfume compositions containing the same.

(2) Description of the Prior Art

There is disclosed 5- or 6-ethylidene-2-hydroxymethylbicyclo[2.2.1]heptane in German Laid-Open Patent Publication No. 3319740. This alcohol is recognized to have spicy, floral and greenish aroma.

In the relevant technical field, however, the development of novel fragrant substances having a variety of different tones are eagerly looked for. The inventors of the present application have thus investigated various compounds. As a result, it was found that the 5-vinyl-2-hydroxymethylbicyclo[2.2.1]heptane and 6-vinyl-2-hydroxymethylbicyclo[2.2.1]heptane are quite useful compounds having strong fragrance that is different form the above known compounds, thereby accomplishing the present invention.

BRIEF SUMMARY OF THE INVENTION

It is, therefore, the primary object of the present invention to provide a novel fragrant substance which gives out a strong odor that is different form those of conventionally known substances.

Another object of the invention is to provide a novel compound of 5- or 6-vinyl-2-hydroxymethylbicyclo[2.2.1]-heptane of the following structural formula (I) and a perfume composition containing the same.

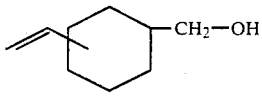
(I)

The compound according to the present invention is a novel compound that has not been known to those skilled in the art. This compound has a particular fragrance of a mint-like note partaking of camphor tone and it can be advantageously used for preparing various kinds of perfumes, cosmetics and toiletries.

DETAILED DESCRIPTION OF THE INVENTION

The vinylnorbornyl alcohol according to the present invention can be prepared from a starting material of 5-vinylbicyclo[2.2.1]-2-heptane (hereinafter referred to as "VBH") that is represented by the following structural formula (II).

(II)

For example, as indicated in the following reaction formula, the compound of the present invention can be prepared by firstly producing 5- or 6-vinyl-2-formylbicyclo[2.2.1]-heptane from VBH and the formyl group of the reaction product is then reduced.

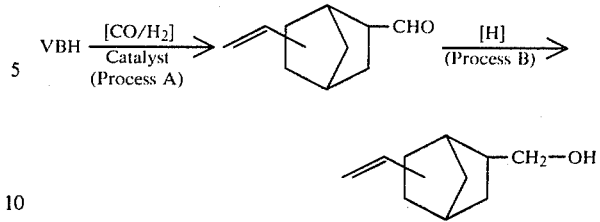

The above Process A is a hydroformylation step which can be carried out in the like manner as the preparation of 5- or 6-ethylidene-2-formylbicyclo[2.2.1]heptane by hydroformylation of 5-ethylidenebicyclo[2.2.1]heptane as disclosed in U.S. Pat. No. 4,524,017.

In the Process A, usable catalysts are exemplified by transition metals such as Pt, Co, Rh, Ru and Ir, and their halides, oxides, carboxylates and nitrates, and their complexes having ligands of phosphines, amines, olefins, carbon monoxide and hydrogen atoms.

More particularly, they are exemplified by $PtH(SnCl_2)[P(C_6H_5)_3]_2$, $Co_2(CO)_8$, $C_6H_5Co_8(CO)_9$, $HCo(CO)_3P(C_6H_5)_3$, $HCo(CO)_3P(n-C_4H_9)_3$, $CH_3CCo_3(CO)_9$, cobalt naphthenate, cobalt octylate, $Rh_4(CO)_{12}$, $HRhCO[P(C_6H_5)_3]_3$, activated $Ru(OH)_3$ and $IrCl(CO)[P(C_6H_5)_3]_2$.

These catalysts can be employed intact or in the carrier-supported form with a solid carrier such as activated carbon, alumina or silica.

The amount of these catalysts used is 0.02 to 0.20 mole per 1 mole of VBH. The reaction temperature is in the range of 30° to 300° C., and preferably 50° to 250° C. The mixing ratio of carbon monoxide to hydrogen is from 1:1 to 1:4, where about 1:1 is preferable. The reaction pressure is usually in the range of 1 to 450 kg/cm².

As a reaction media, hydrocarbons such as pentane, hexane, heptane, benzene and xylene, ethers such as tetrahydrofuran and dioxane, and Y-butyrolactone can be used, however, the reaction can also be carried out without such a reaction medium.

In the foregoing Process B, the alcohol of the present invention is obtained by reducing the 5- or 6-vinyl-2-formylbicyclo[2.2.1]heptane. This process can be also carried out in the like manner as the conventional methods for reducing an unsaturated aldehyde to an unsaturated alcohol.

For example, 5- or 6-vinyl-2-formylbicyclo[2.2.1]-heptane can be easily reduced by using a reducing agent of metal hydride such as lithium aluminum hydride and sodium borohydride which can reduce the aldehyde without exerting any influence on double bonds. More particularly, the reduction is carried out, for example, at temperatures of 0° to 70° C. and at atmospheric pressure with a reaction medium such as water, methanol, ethanol, isopropanol, tetrahydrofuran, 1,2-dimethoxyethane and diglyme, which are properly selected according to the kind of reducing agent used.

After the reduction, the reducing agent is decomposed and the reaction product is extracted with ether, which is followed by distillation at a reduced pressure to obtain the aimed product.

The 5- or 6-vinyl-2-hydroxymethylbicyclo[2.2.1]-heptane according to the present invention can be used intact or by mixing it in an effective amount with other perfume ingredients for perfumes, cosmetics, soaps, detergents, shampoos, waxes, fragrant agents and deodorants.

The novel compound of the invention has a mint-like note partaking of camphor tone which is stronger than and quite different from the odor of the known compound of 5- or 6-ethylidene-2-hydroxymethylbicyclo[2.2.1]heptane.

EXAMPLE 1

Preparation of 5- or 6-vinyl-2-formylbicyclo[2.2.1]heptane:

A 500 ml autoclave was fed with 12.0 g (0.10 mole) of VBH, 3.4 g (0.010 mole) of dicobalt octacarbonyl as a catalyst and 180 ml of Y-butyrolactone as a reaction medium. A mixed gas (1:1) of carbon monoxide and hydrogen was then fed to the autoclave under a pressure of 100 kg/cm$^2$ and reaction was carried out at 140° C. with stirring under the same pressure. After the reaction, the autoclave was cooled and the contents were taken out. The contents were then distilled under reduced pressure to obtain 5- or 6-vinyl-2-formylbicyclo[2.2.1]heptane.
Boiling Point: 62°–63° C./1.0 mmHg
Quantity: 8.5 g (56.7% yield)

Preparation of 5- or 6-vinyl-2-hydroxymethylbicyclo[2.2.1]heptane:

To 50 ml of methanol was added 1.3 g (0.033 mole) of sodium boron hydride and, with stirring at room temperature, 10.0 g (0.067 mole) of the 5- or 6-vinyl-2-formylbicyclo[2.2.1]heptane that was obtained in the like manner as the foregoing process, was added dropwise slowly. After the dropwise addition, the stirring was continued for further 1 hour at about 40° C. The methanol was then distilled off and the remainder was subjected to ether extraction. The ether layer was rinsed with water, then dried and the ether was distilled off. The thus obtained substances was distilled under reduced pressure to obtain colorless transparent oily substance of 5- or 6-vinyl-2-hydroxymethylbicyclo[2.2.1]heptane.
Boiling Point: 62°–66° C./0.6 mmHg
Quantity: 5.2 g (51.1% yield)

| Elemental Analysis (as $C_{10}H_{16}O$): | | |
|---|---|---|
| | C (%) | H (%) |
| Calculated: | 78.9 | 10.6 |
| Found: | 78.7 | 10.9 |
| IR Analysis (liquid film, cm$^{-1}$) | 3650, 3030, 1630 and 1060 | |
| $^1$H-NMR Analysis (medium: CCl$_4$, δ): | | |
| 6.35–5.40 | (multiplet, 1 H) | |
| 5.20–4.70 | (multiplet, 2 H) | |
| 4.35–3.50 | (multiplet, 2 H) | |
| 3.30 | (singlet, 1 H) | |
| 2.30–0.80 | (multiplet, 10 H) | |

FORMULATION EXAMPLE

The 5- or 6-vinyl-2-hydroxymethylbicyclo[2.2.1]heptane obtained in the above Example was a compound having a mint-like note partaking of camphor tone. Using this compound, an oriental rose perfume was prepared according to the following formula:

| Rhodinol | 30 g |
|---|---|
| β-Phenylethyl alcohol | 25 g |
| Bulgarian rose oil | 15 g |

| -continued | |
|---|---|
| Guaiol acetate | 15 g |
| Alcohol prepared in Example | 15 g |
| Total | 100 g |

An aqueous-gel-type odorous agent was prepared by using this formulated perfume and carrageenin gel. This agent was suitable as an oriental rose perfume for interior use.

EXAMPLE 2

In the following experiment, it was clarified that the compound according to the present invention is quite superior to known compounds in view of the intensity of odor (and its nature of long-lasting odor).

METHOD FOR EVALUATING INTENSITY OF ODOR

The panelists were those who have engaged for more than 5 years in the research of manufacturing of odorous substances. They received training for correctly discriminating the intensities of odors of several odorous substance solutions in odorless alcohol of various concentrations.

Test pieces were made by soaking paper sheets with previously prepared samples (solutions of several compounds in ordorless alcohol) and the intensities of odors were evaluated by five panelists. The resultant points were expressed by eleven ranks as follows:
10: Intensity of the same level as camphor
5: Intermediate between camphor and odorless alcohol
0: Intensity of the same level as odorless alcohol
Test conditions were as follows:
Odorous compounds tested:
The compound of the present invention, 5- or 6-ethylidene-2-hydroxymethylbicyclo[2.2.1]heptane and 5- or 6-ethyl-2-hydroxymethylbicyclo[2.2.1]heptane
Concentrations of odorous compounds:
1%, 5% and 10%
Evaluation of odors:
Paper sheets were soaked with the alcohol solutions and alcohol content was spontaneously evaporated. The thus obtained test pieces were evaluated within the same day, after one weak and after one month.

TABLE 1

| | Results of Test: | | | |
|---|---|---|---|---|
| Compounds | Conc. of Solution | Same Day | After 1 Week | After 1 Month |
| 5- or 6-vinyl-2- | 1% | 7.0 | 6.5 | 5.5 |
| hydroxymethylbicyclo- | 5% | 7.5 | 7.0 | 6.0 |
| [2.2.1]heptane | 10% | 8.0 | 8.0 | 7.0 |
| 5- or 6-ethylidene-2- | 1% | 3.0 | 1.5 | 1.0 |
| hydroxymethylbicyclo- | 5% | 3.5 | 2.0 | 1.5 |
| [2.2.1]heptane | 10% | 4.0 | 3.0 | 1.5 |
| 5- or 6-ethyl-2- | 1% | 2.0 | 1.0 | 0.5 |
| hydroxymethylbicyclo- | 5% | 3.0 | 1.5 | 1.0 |
| [2.2.1]heptane | 10% | 3.5 | 2.0 | 1.5 |

Note: In the above data, the averages of 5 panelists' evaluations were rounded at 0.5.

As will be understood from the above results, the compound according to the present invention has quite a good nature of long-lasting odor, and the intensity of odor is also high.

What is claimed is:

1. A vinylnorbornyl alcohol of 5- or 6-vinyl-2-hydroxymethylbicyclo[2.2.1]heptane which is represented by the following structural formula (I):

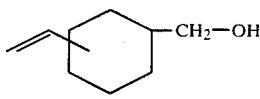
(I)
2. A perfume composition containing an effective amount of 5- or 6-vinyl-2-hydroxymethylbicyclo[2.2.1-]heptane which is represented by the following structural formula (I):
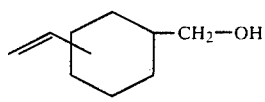
(I)
* * * * *

UNITED STATES PATENT AND TRADEMARK OFFICE
CERTIFICATE OF CORRECTION

PATENT NO. : 4,693,844

DATED : September 15, 1987

INVENTOR(S) : Yoshiharu Inoune, et al.

It is certified that error appears in the above-identified patent and that said Letters Patent is hereby corrected as shown below:

Column 1, line 40: " 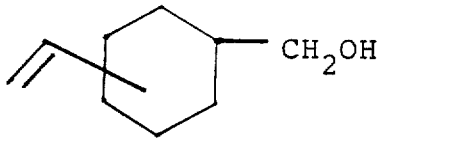 "

should read as -- 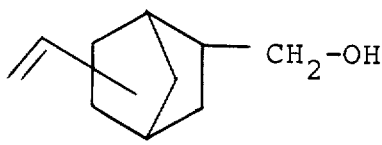 --

Column 2, line 38: "As a reaction media" should read as --As reaction media--

Column 2, line 40: "Y-butyrolactone" should read as -- γ-butyrolactone--

Column 3, line 15: "Y-butyrolactone" should read as -- γ- utyrolactone--

UNITED STATES PATENT AND TRADEMARK OFFICE
CERTIFICATE OF CORRECTION

PATENT NO. : 4,693,844

DATED : September 15, 1987

INVENTOR(S) : Yoshiharu Inoune, et al.

It is certified that error appears in the above-identified patent and that said Letters Patent is hereby corrected as shown below:

Column 3, line 39: "The thus obtained substances was" should read as --The thus obtained substance was--

Column 4, line 46: "after one weak" should read as --after one week--

Column 4, line 47: "Results of Test" should be inserted before "Table I"

Column 5, line 1: " 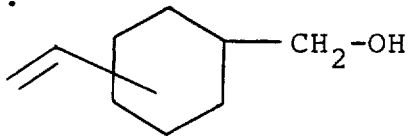 "

should read as -- 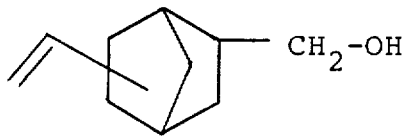 --

UNITED STATES PATENT AND TRADEMARK OFFICE
CERTIFICATE OF CORRECTION

PATENT NO. : 4,693,844
DATED : September 15, 1987
INVENTOR(S) : Yoshiharu Inoune, et al.

It is certified that error appears in the above-identified patent and that said Letters Patent is hereby corrected as shown below:

Column 6, line 3: " 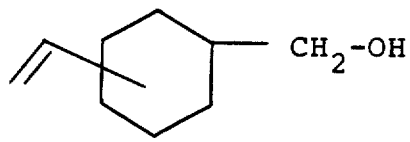 "

should read as -- 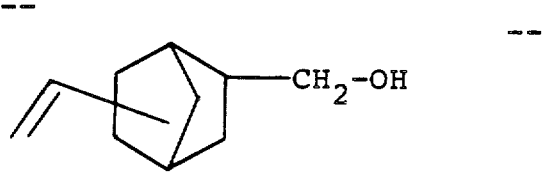 --

Signed and Sealed this

Eighth Day of March, 1988

Attest:

DONALD J. QUIGG

Attesting Officer　　　　Commissioner of Patents and Trademarks